United States Patent [19]

Buffington et al.

[11] 4,426,357

[45] Jan. 17, 1984

[54] ANTIBODY ELUTION REAGENT KIT

[75] Inventors: Sherry Buffington, Ringoes; Leonard T. Wilson, Verona, both of N.J.

[73] Assignee: Ortho Diagnostic Systems Inc., Raritan, N.J.

[21] Appl. No.: 300,707

[22] Filed: Sep. 9, 1981

[51] Int. Cl.³ .............................................. G01N 33/54
[52] U.S. Cl. ...................... 422/61; 436/520; 436/547; 436/808
[58] Field of Search ...................... 23/230 B; 252/408; 424/12; 422/61; 436/520, 547, 808

[56] References Cited

U.S. PATENT DOCUMENTS 3,171,752  3/1965  Rankin ................................. 106/194
4,051,260  9/1977  Nelson et al. ....................... 424/331
4,177,257  12/1979  Hodson et al. ................... 424/45 X

OTHER PUBLICATIONS

Blood Transfusion in Clinical Medicine, by Mollison, 6th Edition, Jan. 1979, Blackwell Scientific Publications, pp. 479-480.
Bueno et al., Transfusion, vol. 21, No. 2, pp. 157-162, Mar.-Apr. 1981.

*Primary Examiner*—Arnold Turk
*Attorney, Agent, or Firm*—Mark A. Hofer

[57] ABSTRACT

A reagent kit for eluting antibodies present on the surface of red blood cells comprises sorbitan trioleate or other variants within the sorbitan family and a red blood cell diluent as well as methods for use.

2 Claims, No Drawings

ANTIBODY ELUTION REAGENT KIT

FIELD OF THE INVENTION

This invention relates to a reagent kit and methods for its use for the elution of antibodies from the surface of red blood cells.

BACKGROUND OF THE INVENTION

In accordance with well known procedures it is often necessary to determine the cause of a positive direct antiglobulin test performed in the clinical laboratory. Such a determination requires, in part, the isolation of antibodies present on the surface of red blood cells for a determination of their specificity. The process of disassociation of the antibody from the red cell is referred to as elution and the active material for performing this process is the eluting agent. Typically, the antibodies are disassociated from the surface of the red blood cells by the eluting agent and can be subsequently isolated from the eluate.

The collection of antibodies coating the red blood cells in vivo is often essential for the identification and subsequent diagnosis of autoimmune hemolytic anemia, hemolytic disease of the newborn or other suspected hemolytic-type diseases following transfusion reactions. Elution techniques also permit the demonstration of weakly expressed antigens on red blood cells such as those in subgroups of A or B blood types following an in vitro sensitization with an appropriate antibody. Further, elution procedures permit the separation and isolation of individual specificities of antibody mixtures following adsorption in vitro with selected blood cells. Elution procedures are of further utility in the preparation of antisera free of unwanted antibodies following in vitro adsorption with red cells of appropriate phenotype. Elution procedures are further finding increased pharmacological use in the confirmation of sensitization of red blood cells by certain drugs.

The classical method of elution is that of Landsteiner and Miller, described in *Blood Transfusion in Clinical Medicine* by Mollison, Sixth Edition, January 1979. The Landsteiner et al method simply involved heating the red blood cells to 56° C. in order to remove and recover antibody adsorbed onto the cells at room temperature. Typically, serum was added to the cell suspension and incubated at room temperature in order to sensitive the cells. The cells were then collected by centrifugation, resuspended with saline, and placed in a water bath at 56° C. for five minutes with repeated shaking. Centrifugation of the mixture resulted in a supernatant fluid, or eluate, containing the antibodies. The advantages of this system were numerous; it was inexpensive, easily performed without the requirements of pH adjustments, the eluate remained on top of the cells following centrifugation and a substantial portion of the cell population remained undamaged permitting further elution procedures. Landsteiner's system did, however, require 6% bovine serum albumin and a 56° C. heat source. Further, the method was often incapable of removing for detection antibodies weakly coating the cells. The system also required rapid removal of the eluate in order to prevent potential reassociation of the antibody with available antigenic sites present on the cells.

Subsequent efforts to increase the sensitivity resulted in Rubin's ether elution method, also described in *Blood Transfusion in Clinical Medicine*, supra. The method required mixing washed and packed red blood cells with an equal volume of 0.8% sodium chloride followed by the addition of two volumes of diethylether in a stoppered container. The container was repeatedly inverted for one minute and then centrifuged for 10 minutes. The top layer of ether was aspirated and the middle layer, containing denatured stroma, was also removed. The bottom layer contained the antibodies of interest. Rubin's ether method successfully provided a good yield as well as an eluate capable of frozen storage in excess of three months without loss of reactivity. The Rubin ether method presented numerous disadvantages however, not the least of which was the use of a potentially explosive compound producing an extreme fire hazard and necessitating explosion proof storage means as well as fume hoods and proper disposal pursuant to OSHA regulations. The procedure further required the careful removal of all residual ether from the final eluate in order to prevent subsequent lysing of reagent red blood cells. Additionally, the great expense associated with the Rubin ether procedure makes this procedure undesirable for large scale clinical testing.

A class of commercially available reagents is known by those in the art as the digitonin/acid method. This method provides for hemolyzation of the red blood cells by digitonin to produce intact stroma free of hemoglobin and capable of ready sedimentation. Typically the stroma is eluted with 0.1 molar glycerin buffer at a pH of three in order to produce a clear eluate. Although the procedure is specific and reliable, it generally requires more steps and larger amounts of reagents. Further, pH correction is critical since any residual reagent may lyse reagent red blood cells subsequently used in specificity testing. The time consuming and complicated nature of the procedure further reduces its effectiveness in clinical applications. R. Bueno, et al presented, in the March-April 1981 edition of *Transfusion*, an article entitled "Elution of Antibody from Red Blood Cells Using Xylene—A Superior Method". It is claimed that the xylene method was superior to the ether method because it yielded stronger eluates. The method requires the mixture of one volume of sensitized packed red blood cells, one volume of saline, and two volumes of xylene in a stoppered test tube. The mixture is agitated for a minute and then incubated at 57° C. for 10 minutes with occasional mixing. Centrifugation of the mixture at 1000 g for five minutes yields three distinct layers wherein the upper layer containing xylene and the middle layer containing stroma are removed. Additionally, it has been found necessary to remove the top portion of the third eluate layer containing the antibodies. Removal of the stroma layer requires great care in order to avoid contamination of the eluate. An additional disadvantage, characteristic of the xylene method, is the requirement for extensive care in handling since xylene is a toxic aromatic hydrocarbon requiring a fume hood and proper disposal since it presents an explosive hazard. Further, the cost of xylene makes it prohibitive for many routine clinical applications.

OBJECTS AND SUMMARY OF THE INVENTION

It is an object of the present invention to provide an eluting reagent kit which avoids the problems associated with toxic and/or explosive materials. It is a further object to provide a reagent kit which may be economically used in large scale clinical applications. It is a further object to provide a reagent kit which avoids critical tolerances with respect to pH control and precise volume requirements. It is a yet further object to provide an antibody eluting reagent kit and methods for use to meet all the above objects and which is capable of providing a sensitivity substantially equal to that of the presently available reagents and methods.

In accordance with the stated objects, there is provided a reagent kit for eluting antibodies present on the surface of red blood cells comprising an ester selected from the group consisting of sorbitan trioleate, sorbitan monoleate, and sorbitan monolaureate; and a red blood cell diluent selected from the group consisting of saline, buffered saline, bovine serum albumin, and buffered red cell diluent. The preferred embodiment of the reagent kit comprises sorbitan trioleate and buffered red cell diluent. Additionally provided is a method for eluting antibodies present on the surface of red blood cells comprising: providing an aqueous suspension of red blood cells, combining with said aqueous suspension of red blood cells an eluting reagent selected from the group consisting of sorbitan trioleate, sorbitan monoleate, and sorbitan monolaureate; agitating said combination in the presence of heat; centrifuging said combination; and removing the aqueous portion of said combination containing the eluted antibodies. The preferred embodiment of this method provides for sorbitan trioleate as the eluting reagent. Additionally provided is a method of eluting antibodies present on the surface of red blood cells present in a liquid sample comprising: centrifuging the sample and removing the liquid; combining with the centrifuged red blood cells a red cell diluent and an ester selected from the group consisting of sorbitan trioleate, sorbitan monoleate, and sorbitan monolaureate; agitating and heating said combination; centrifuging said agitated combination; and collecting the red cell diluent portion of the centrifuged combination containing the eluted antibodies. Alternative embodiments provide for the red cell diluent to be selected from the group consisting of saline, buffered saline, bovine serum albumin, and buffered red cell diluent. In a preferred embodiment of the above method, the red cell diluent is buffered red cell diluent and the ester is sorbitan trioleate. The most preferred method provides for the volume of red blood cells to be one-half an ml, the volume of buffered red cell diluent to be one and one-half mls and the volume of sorbitan trioleate to be three mls.

PREFERRED EMBODIMENTS OF THE INVENTION

The elution procedure for the disassociation of antibody from red cells is preferably performed following a thorough washing of the antibody sensitized red blood cells with isotonic saline in order to ensure complete removal of unadsorbed antibody. Thereafter a buffered red cell diluent which serves as the eluate solution and an eluting agent are added to the packed red blood cells following centrifugation, and the mixture is agitated in a 56° C. to 60° C. water bath to accomplish cell lysis. It has been found preferable to employ a 60° C. water bath when using sorbitan trioleate as the eluting agent in order to maximize the yield of eluted antibody. The heated mixture is then centrifuged and the eluate separated from the stroma and the eluting agent. The eluate, containing the disassociated antibodies, is then tested for specificity.

The reagent kit for eluting antibodies ideally contains two vials, one containing buffered red cell diluent and the other containing, preferably, sorbitan trioleate. Tyically, the kit may be stored unopened at room temperature and at 2° C. to 8° C. after opening. Freezing is advantageously avoided and turbidity within either vial may be indicative of product deterioration or alteration. Although no special preparation of the patient is required prior to collection of the blood sample, ideally, the blood is collected by an approved medical technique and tested while still fresh. Storage of the blood sample at 2° C. to 8° C. for up to seven days permits testing at some time subsequent to collection. In order to provide a sufficient volume of red cells for the procedure, an anticoagulated specimen is preferred; the anticoagulant of choice is EDTA. Acceptable substitutes for EDTA include ACD, CPD, oxylate and heparin. Although an anticoagulated specimen is preferred, the reagent kits and methods provided are sufficiently flexible to permit application to clotted specimens.

Proper use of the provided procedures requires cognizance of the inherent limitations. As with all methods, insufficient washing of sensitized cells may cause erroneous results due to the presence of antibodies present in the whole blood solution but not adsorbed to the red blood cells. Further, a positive direct antiglobulin test may be due solely to complement bound to the red cells and would therefore be expected to normally yield an unreactive eluate. When eluting red blood cells with a positive direct antiglobulin test due to drug sensitization, an eluate with no apparent activity may result unless cells coated with the appropriate drug are also included in the eluate testing. Further considerations in cases of red blood cells sensitized in vitro by adsorption include serum-to-cell ratio, temperature and length of incubation, as well as the number, type and accessability of red cell antigens.

EXAMPLE

The following example demonstrates the employment of washing procedures in conjunction with the preferred method of antibody elution.

A one to two ml quantity of whole blood is transferred into a 13×100 mm test tube and centrifuged. The supernatant is discarded and the resulting packed red cells are washed 6 times using large volumes of isotonic saline. Following the sixth wash, a volume of isotonic saline equal to the volume of packed cells is added to the test tube and mixed thoroughly. It is preferred that this suspension be transferred into a clean 13×100 mm test tube in order to avoid the possible elution of antibody adsorbed to the glass. The suspension is then centrifuged and the supernatant saline transferred into a tube labelled "last wash" to be tested later with the eluate. One and one-half mls of buffered red cell diluent and 3 mls of sorbitan trioleate are added to the final packed cell volume. The tube is stoppered and mixed by rapid inversion and then agitated constantly in a 56° C. to 60° C. water bath for 7 minutes. If agitation cannot be consistently supplied, the incubation time is extended to 10 minutes. The mixture is then centrifuged at 3400 RPM for 5 minutes and the eluate present at the bottom of the test tube is removed with a Pasteur pipette. The eluate is then centrifuged again at 3400 RPM for 2 minutes and any residual eluting solution aspirated off. The eluate as well as a control aliquot from the last wash are ready for testing for antibody specificity. Activity in the last wash is generally indicative of insufficient washing indicating the advantageous repetition of the elution procedure in order to obtain the most satisfactory results.

Typically the eluate is tested against a panel of red cells. After the addition of antiglobulin serum, the appearance of agglutination is indicative that antibody has been recovered. Conversely, the absence of agglutination demonstrates a failure to recover antibody from the red cells.

In accordance with the knowledge of those skilled in the art, numerous alternatives will become apparent without departing from the spirit or scope of the present invention.

What is claimed is:

1. A reagent kit for eluting, in the presence of heat and agitation, antibodies present on the surface of red blood cells consisting essentially of:
   a first container containing an ester selected from the group consisting of sorbitan trioleate, sorbitan monoleate, and sorbitan monolaureate; and
   a second container containing a red blood cell diluent selected from the group consisting of saline, buffered saline, bovine serum albumin, and buffered red cell diluent.

2. A reagent kit for eluting, in the presence of heat and agitation, antibodies present on the surface of red blood cells consisting essentially of:
   a first container containing an effective amount of sorbitan trioleate for disassociating substantially all adsorbed antibodies from the cells' surface and a second container containing buffered red cell diluent.

* * * * *